United States Patent [19]
Wegner et al.

[11] Patent Number: 4,601,986
[45] Date of Patent: Jul. 22, 1986

[54] PROTEIN PRODUCT OF REDUCED NUCLEIC ACID CONTENT AND LOW ALLERGENICITY

[75] Inventors: Eugene H. Wegner; Lucas K. Shay, both of Bartlesville, Okla.

[73] Assignee: Phillips Petroleum Company, Bartlesville, Okla.

[21] Appl. No.: 518,778

[22] Filed: Jul. 29, 1983

[51] Int. Cl.$^4$ .......................... C12N 1/16; A23L 1/28
[52] U.S. Cl. .................... 435/255; 435/253; 435/256; 435/804; 426/60; 426/656
[58] Field of Search ................. 426/60, 431, 655, 656; 435/91, 172, 251, 253, 255, 256, 804

[56] References Cited

U.S. PATENT DOCUMENTS

| | | | |
|---|---|---|---|
| 2,809,113 | 10/1957 | Stimpson et al. | 426/41 |
| 3,266,901 | 8/1966 | Faustini et al. | 424/114 |
| 3,585,179 | 6/1971 | Samejima | 260/12 R |
| 3,615,654 | 10/1971 | Ayukawa et al. | 426/262 |
| 3,720,585 | 3/1973 | Tannenbaum et al. | 435/270 |
| 3,809,776 | 5/1974 | Chao | 426/431 |
| 3,821,080 | 6/1974 | Kalina et al. | 435/270 |
| 3,833,552 | 9/1974 | Akin | 260/112 R |
| 3,845,222 | 10/1974 | Tannenbaum | 426/456 |
| 3,862,112 | 1/1975 | Ishida et al. | 260/112 R |
| 3,878,093 | 4/1975 | Kanani et al. | 435/253 |
| 3,885,050 | 5/1975 | Ridgway, Jr. et al. | 426/60 |
| 3,891,772 | 6/1975 | Ridgway, Jr. et al. | 126/60 |
| 3,903,314 | 9/1975 | Chao | 426/656 |
| 3,925,562 | 12/1975 | Tannenbaum | 426/276 |
| 3,947,605 | 3/1976 | Chao | 426/656 |
| 3,960,659 | 6/1976 | Fazakerley | 267/25 |
| 3,968,009 | 7/1976 | Tannenbaum et al. | 435/270 |
| 4,021,303 | 5/1977 | Nakabayashi | 435/317 |
| 4,054,679 | 10/1977 | Meleer et al. | 426/656 |
| 4,079,048 | 3/1978 | Chao | 260/112 R |
| 4,133,904 | 1/1979 | Steer et al. | 426/656 |
| 4,192,897 | 3/1980 | Kajinami et al. | 426/60 |
| 4,293,575 | 10/1981 | Cockram et al. | 426/102 |

FOREIGN PATENT DOCUMENTS

| | | |
|---|---|---|
| 719328 | 9/1967 | Belgium . |
| 1071338 | 2/1980 | Canada . |
| 1161229 | 8/1969 | United Kingdom . |

OTHER PUBLICATIONS

Stewart & Russell, *Critical Reviews in Biotechnology*, vol. 1, Issue 1 (1983), pp. 34–37, 55, 56.

Nature, vol. 228, Oct. 10, 1970, p. 181 "New Process for Reducing the Nucleic Acid Content of Yeasts"—Maul, Sinskey, & Tannenbaum.

Castro et al., "Reduction of Nucleic Acid Content in Candida Yeast Cells by Bovine Pancreatic Ribonuclease A Treatment," *Applied Microbiology*, vol. 22, No. 3, Sep. 1971, pp. 422–427.

Dillan, "Toxicological and Immunological Studies of New Single Cell Protein in Human Subjects", M.I.T. Ph.D. Thesis, M.I.T. Dept. of Nutrition and Food Science (1976), pp. 12, 22–23, 26, 58–60, 68, 78, 99, & 122.

Kinsella, "Functional Properties in Novel Proteins", *Chemistry and Industry* Mar. 5, 1977, pp. 177–182.

Kinsella, "Functional Properties of Proteins in Foods: A Survey", *CRC Crit. Rev. Food Sci. Nutri.* 1, pp. 219–280 (1976).

Kinsella et al., "Yeast Proteins: Recovery, Nutritional and Functional Properties", *Adv. Exp. Med. Biol.* 105, pp. 797–825 (1978).

Nesmeyanov et al., "Isolation of Food-Acceptable Compounds from Hydrocarbon-Cultivated Yeasts and the Use of These Compounds for Preparing Food-Grade Products", *Proceedings of the 8th World Petroleum Congress*, vol. 5 (1971) pp. 141–148.

Phua, "Safety of Single-Cell Protein for Human Feeding: The Development of Immunological Assays for Allergens in Some Single-Cell Proteins", M.I.T. Ph.D. Thesis, M.I.T. Dept. of Nutrition and Food Science (1981) pp. 45, 50, 89, 89a, 91, 121, 124–125.

Scrimshaw et al., "The Nutritional Value and Safety of Single-Cell Protein for Human Consumption", copy of talk given at the Paris SCP Symposium Jan. 1981.

Vananuvat et al., "Some Functional Properties of Protein Isolates from Yeast, *Saccharomyces fragilis*," *J. Agri. Food* 23 Jul./Aug. 1975, pp. 613–616.

Zee et al., "Simple Process for the Reduction in the Nucleic Acid Content in Yeast," *Applied Microbiology*, vol. 29, No. 1, Jan. 1975, pp. 59–62.

*Primary Examiner*—David M. Naff
*Assistant Examiner*—William J. Herald
*Attorney, Agent, or Firm*—Lyell H. Carver

[57] ABSTRACT

A nucleic acid-reduced substantially allergen-free single cell protein product is obtained by culturing a yeast, fungi or bacterium on an ultra-low sulfate medium, treating the produced cells with a base at a pH of about 9.5 with moderate heat, thereafter treating the base-treated cells with acid to a pH of about 4 with moderate heat, and treating the base-treated acid-treated cells with a relatively high temperature short time heat shock, followed by extrusion. Optionally, the extruded product is annealed.

14 Claims, No Drawings

PROTEIN PRODUCT OF REDUCED NUCLEIC ACID CONTENT AND LOW ALLERGENICITY

FIELD OF THE INVENTION

The invention pertains to improved protein products of reduced nucleic acid content and reduced allergenicity. In another aspect, the invention pertains to methods to reduce nucleic acid and allergen content of protein derived from single cell microorganisms.

BACKGROUND OF THE INVENTION

Microbial cells have high potential as protein sources, being relatively cheaply grown on a wide variety of substrates, paraffins, oxygenated hydrocarbons such as alcohols, biomass, and the like. Numerous investigations and developments continue.

The natural or inherent nucleic acid content of protein from microbial cells, while high, is not objectionable for almost all animals. However, such proteins can only be used in very limited amounts by humans without reduction in nucleic acid content.

As is known, nucleic acid is metabolized by human beings but breaks down to uric acid. Uric acid is a potential problem when large amounts of nucleic acid-containing microbial cells are ingested by humans, since uric acid is far less soluble than is the normal end product of protein metabolism, urea. Buildups of uric acid may result in gout or other problems. Many patents and articles have issued describing various methods of nucleic acid reduction.

Even when the nucleic acid content is reduced to more tolerable levels, still, some human beings persistently exhibit allergic reactions to ingestion of the microbial cell derived protein.

"Allergy" simply means a hypersensitivity to a particular material, or component thereof. Many foods result in "allergy" in various people, and almost any commonly used food today results in some allergic response to at least a few individuals. And, of course, the greater the relative consumption of any single food per kilo of body weight, the greater the likelihood of allergic responses to show up within a given population.

Reduction in allergen content of microbial cell derived protein has proven particularly difficult. Since a single cell protein product frequently is intended to be consumed as an additive with other food, its presence as an additive may not be readily recognized and avoided by individuals who may be sensitive to it. Thus, it is imperative that the frequency of such allergic responses be kept low.

The adverse reactions to single cell protein materials usually fall into two broad categories, gastro-intestinal symptoms, and cutaneous symptoms. The onset of adverse symptoms may not be immediate, but may in some cases be delayed from two to as much as thirty days from the start of consumption according to Phua (M.I.T. Thesis 1981, page 11).

For single cell protein materials, it is not expected to eliminate all "allergens" to the effect that no human being will have any response at any time. What is needed, however, is a minimization of allergic responses by finding a broadly applicable method of reducing both nucleic acid and "allergens", applicable to microbial cells, and without destroying the food quality of the protein.

BRIEF SUMMARY OF THE INVENTION

Rather than viewing the problem as one simply of "allergen" removal, we studied the entire sequence of the production of microbial derived protein.

We discovered a process of producing microbial cellular protein, from yeasts, fungi, or bacteria, by a method that results in a product of low nucleic acid and minimal allergen content (minimum human hypersensitivity reaction). The process of our invention briefly comprises:

(1) growing single cell microorganisms on ultra-low sulfur medium, under aerobic aqueous fermentation conditions, employing a suitable carbon energy substrate;

(2) treating the crude microbial cells therefrom with a base at an elevated pH with heat;

(3) treating the base treated cells with acid to a low pH with heat;

(4) heat-shocking the so-treated cells at elevated temperatures for a very short time; and (5) extruding the cells under heat and pressure.

We have discovered that it is essential to control the entire sequence of operation, beginning with the medium itself in which the cells grow, followed by a specific sequence of treatments. The product resulting from this series of steps has very low nucleic acid content, exhibits very low allergenicity, and thus can be consumed in reasonable quantities for long intervals by humans without known serious problems.

In accordance with our invention, yeasts, fungi, or bacteria are grown on what we term a "ultra-low sulfur medium", employing a carbon energy source (substrate), under aerobic aqueous fermentation conditions. The carbon energy substrate can be any carbon energy source, such as n-paraffins, oxygenated hydrocarbons including various carbohydrates, available biomass, and the like, suitable as substrates. It is recognized that particular strains do vary in their preference for various substrates.

To avoid handling large quantities of aqueous liquor unnecessarily, the cells preferably are grown at high cell densities to produce directly from the fermentor a cellular cream of concentrated cells which can be directly used in the base-treatment step. The fermentor effluent, the aqueous ferment containing cells produced under lower cell density fermentations, can be concentrated where needed by suitable techniques before being treated with a base. Alternatively, the cells can be separated from the aqueous ferment, optionally dried, and resuspended in fresh water to the desired cream strength.

The cells as a cream are exposed to a pH in the range of about 7 to 10, accompanied with heat in the range of about 65° C. to 99° C., for a moderate time of about 30 to 60 minutes. The cells then are separated from the suspension. The separated aqueous alkaline liquor can be discarded, reused, or recycled to the fermentor.

The alkaline-treated cells are resuspended in water to a cream concentration, treated with dilute acid to a pH of about 3 to 4.5 accompanied with heat to a temperature in the range of about 75° C. to 95° C., for a time of about 30 to 60 minutes. The cells are separated from the acidic liquor. The acidic liquor can be discarded, reused, or recycled as may be convenient.

The resulting now alkaline and acid-treated cells are resuspended in water to the cream concentration, and subjected to short-time heat-shock at a temperature of about 100° C. to 150° C. for a time of about 30 to 120 seconds.

The heat-shocked cells are concentrated to a cell paste. Alternatively, the cells can be separated, dried, and then reconstituted as a paste. The paste is extruded under suitable temperature and pressure conditions.

A further, optional, time-tempering step can be applied for further reduction in allergen content.

DETAILED DESCRIPTION OF THE INVENTION

Medium

The medium employed is an ultra-low sulfur mineral medium. One example of an ultra-low sulfur growth medium is given in Example II herein infra.

An ultra-low sulfur growth medium comprises one in which the sulfur content of the growth medium is kept below about 0.44, more preferably below about 0.40, expressed as grams of sulfur per liter of aqueous ferment. Aqueous ferment is the total of both the aqueous phase and the suspended cellular phase in the fermentor.

Minerals employed include non-sulfate but water-soluble compounds of potassium and magnesium, such as potassium hydroxide, potassium nitrate, potassium phosphate, potassium acetate, magnesium hydroxide, magnesium nitrate, and magnesium acetate. Preferred are potassium hydroxide and magnesium hydroxide for their low cost and ready availability.

The mineral medium preferably and conveniently is employed as a primary mineral medium containing compounds of potassium, phosphorus, magnesium and calcium; and a trace mineral medium containing salts of iron, zinc, copper, and manganese. Optionally other compounds such as boric acid as a source of boron, and potassium iodide as a source of iodine, can be added.

Microorganisms

Suitable microorganisms include any of the fungi, yeasts, or bacteria.

Species of yeasts and fungi include species from the genera Candida, Hansenula, Neurospora, Rhodotorula, Torulopsis, Saccharomyces, Schizosaccharomyces, Pichia, Debaryomyces, Kluyveromyces, Lipomyces, Cryptococcus, Nematospora, and Brettanomyces, Examples include:

| | |
|---|---|
| *Candida boidinii* | *Candida mycoderma* |
| *Candida utilis* | *Candida stellatoides* |
| *Candida robusta* | *Candida claussenii* |
| *Candida rugosa* | *Brettanomyces petrophilium* |
| *Hansenula minuta* | *Hansenula saturnus* |
| *Harsenula californica* | *Hansenula mrakii* |
| *Hansenula silvicola* | *Hansenula polymorpha* |
| *Hansenula wickerhamii* | *Hansenula capsulata* |
| *Hansenula glucozyma* | *Hansenula henricii* |
| *Hansenula nonfermentans* | *Hansenula philodendra* |
| *Torulopsis candida* | *Torulopsis bolmii* |
| *Torulopsis versatilis* | *Torulopsis glabrata* |
| *Torulopsis molishiana* | *Torulopsis numodendra* |
| *Torulopsis nitratophila* | *Torulopsis pinus* |
| *Pichia farinosa* | *Pichia polymorpha* |
| *Pichia membranaefaciens* | *Pichia pinus* |
| *Pichia pastoris* | *Pichia trehalophila* |
| *Neurospora crassa* | *Rhodotorula rubra* |
| *Saccharomyces cerevisiae* | *Saccharomyces fragilis* |
| *Saccharomyces rosei* | *Saccharomyces acidifaciens* |
| *Saccharomyces elegans* | *Saccharomyces rouxii* |
| *Saccharomyces lactis* | *Saccharomyces fractum* |
| *Schizosaccharomyces pombe* | |

Species of bacteria include species from the genera Bacillus, Escherichia, Streptomyces, Micromonospora, Streptoverticillium, Nocardia, Pseudomonas, Methanomonas, Pnotaminobacter, Methylococcus, Arthnobacter, Methylomonas, Brevibacterium, Acetobacter, Micrococcus, Rhodopseudomonas, Corynbacterium, and Microvacterium. Examples include:

| | |
|---|---|
| *Bacillus subtilis* | *Brevibacterium roseum* |
| *Bacillus pumilis* | *Brevibacterium lactofermentum* |
| *Bacillus globigii* | *Brevibacterium ketoglutamicum* |
| *Bacillus niger* | *Bacillus nato* |
| *Escherichia coli* | *Bacillus amyloliquefaciens* |
| *Pseudomonas methanolica* | *Bacillus atenimus* |
| *Pseudomonas orvilla* | *Bacillus licheniformis* |
| *Pseudomonas fluorescens* | *Pseudomonas ligustri* |
| *Pseudomonas oleovorans* | *Pseudomonas methanica* |
| *Pseudomonas boreopolis* | *Pseudomonas aeruginosa* |
| *Pseudomonas methylphilus* | *Pseudomonas putida* |
| *Pseudomonas acidovorans* | *Pseudomonas pyocyanes* |
| *Pseudomonas aerogenes* | *Pseudomonas brevis* |
| *Corynebacterium simplex* | *Pseudomonas methanoloxidans* |
| *Corynebacterium alkanum* | *Protaminobacter ruber* |
| *Streptomyces aureofaciens* | *Corynebacterium hydrocarbooxydans* |
| *Streptomyces rimosus* | *Corynebacterium oleophilus* |
| *Streptomyces coelicolor* | *Corynebacterium glutamicum* |
| *Streptomyces griseus* | *Corynebacterium dioxydans* |
| *Streptomyces cyaneus* | *Micrococcus cerificans* |
| *Streptomyces venezuelae* | *Arthrobacter rufescens* |
| *Corneybacterium hydrocarboclastus* | *Arthrobacter simplex* |
| *Corneybacterium viscosus* | *Methanomonas methanica* |
| *Micrococcus rhodium* | *Methylomonas agile* |
| *Arthrobacter parafficum* | *Methylomonas rubrum* |
| *Arthrobacter citreus* | *Nocardia minimum* |
| *Methanomonas methanoxidans* | *Nocardia butanica* |
| *Methylomonas albus* | *Microbacterium ammoniaphilum* |
| *Methylomonas methanolica* | *Brevibacterium butanicum* |
| *Nocardia salmonicolor* | *Brevibacterium flavum* |
| *Nocardia corallina* | *Brevibacterium paraffinolyticum* |
| *Rhodopseudomonas capsulatus* | *Brevibacterium insectiphilium* |

Presently preferred are yeasts, and of these of the Candida, Saccharomyces and Pichia genera, of these particularly *Saccharomyces cerevisiae, Candida utilis,* and *Pichia pastoris,* such as *Pichia pastoris* NRRL Y-11430 and Y-11431.

Fermentation Conditions

The microorganisms are grown under aerobic aqueous fermentation conditions in the presence of molecular oxygen, a carbon energy substrate, the ultra-low sulfur mineral medium, and an assimilable nitrogen source. Various types of fermentation processes and fermentors known in the art can be utilized. Fermentation can be by a batch-mode, but preferably is continuous. A fermentor such as the foam-filled fermentor as described in U.S. Pat. No. 3,982,998 can be used.

Oxygen can be supplied as air or oxygen-enriched air. The assimilable nitrogen source can be any organic or inorganic nitrogen-containing compound capable of providing nitrogen for metabolic utilization by the growing and reproducing organisms, such as proteins, amino acids, urea, ammonia, ammonium hydroxide, ammonium nitrate, and the like. Ammonia is preferred for economy as well as for pH control.

The growth and reproduction of the microorganism is sensitive to the operating temperature of the aqueous ferment, and each particular microorganism species has an optimum temperature. Exemplary fermentation temperatures are in the range of about 20° C. to 60° C.

Fermentation pressures generally are in the range of about 0.1 to about 100 atmospheres (about 10 to 10,100 kPa), more usually about 1 to 30 atmospheres (about 101 to 3,040 kPa), and more preferably about 1 to 5 atmospheres (101 to 507 kPa) since the higher pressures mean a greater level of dissolved oxygen in the aqueous medium and usually higher productivities.

Carbon Energy Substrate

It is feasible to employ n-paraffins of such as 10 to 20 carbon atoms per molecule, though presently less preferred where single cells are the desired product for food purposes due to the difficulties sometimes encountered in removing residual water-insoluble substrate from the microbial cells. The n-paraffins typically include such as decane, undecane, dodecane, tridecane, tetradecane, pentadecane, hexadecane, octadecane, eicosane, and the like, and mixtures thereof.

The presently more preferred substrates for aqueous fermentation are the carbon-oxygen-hydrogen (C—O—H) compounds of significant water-solubility. Useful C—O—H compounds include the water-soluble carbohydrates, as well as those alcohols, ketones, esters, acids, and aldehydes, and mixtures, which are reasonably significantly water-soluble in character, generally of 1 to 20 carbon atoms per molecule. The more suitable C—O—H compounds hydrocarbons are those of substantially greater water-solubility of up to about 10 carbon atoms per molecule, and the water-soluble carbohydrates generally.

Exemplary carbohydrates include glucose, fructose, galactose, lactose, sucrose, starch, dextrin, and the like, alone or in admixture. Examples of other types of C—O—H compounds include methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and the like, as well as mixtures thereof.

Presently more preferred are the water-soluble alcohols of 1 to 4 carbon atoms, water-soluble acids of 2 to 4 carbon atoms, and the water-soluble carbohydrates. Most preferred at present are the water-soluble monohydric aliphatic hydrocarbyl alcohols, other than 2-methyl-1-propanol which is inhibitory to some yeasts.

Presently most preferred are methanol and ethanol due to the lower relative costs as feedstocks. Conveniently, the methanol or ethanol is added and fed with the trace mineral medium as described hereinabove.

It is presently preferred that the ratio of the carbon energy substrate:aqueous mineral salts medium be in a volume ratio of about 0.5:99.5 to 50:50, more preferably about 10:90 to 50:50, for most effective cellular production for most microorganisms.

Resulting Cells (SCP)

The single cell protein (SCP), the cells produced, on ultra low sulfur medium (ULS) have a lower cellular sulfur content than cells produced on conventional medium. It is presently presumed that this is due to a lower S-containing protein content in the cells cultured on ULS medium. It is presently believed, subject to feeding-tolerance tests, that a desirable sulfur content in ULS-produced cells is in the range of about 0.2 to 0.5 weight percent sulfur as S based on separated, washed, and dried cells.

Post-Treatment

Base-Treatment

The aqueous ferment exiting the fermentation step contains both supernatant aqueous liquor and suspended cells.

The cells for treatment with base are treated as a cellular cream containing predominantly water and having a solids content of about 10 to 25 weight percent, preferably about 10 to 20 weight percent. The aqueous ferment containing the cells is either concentrated to remove a portion of the mother liquor such as by centrifugation, or if from a high salts high cell fermentation are obtained in a sufficiently concentrated cream form. Reducing the amount of aqueous liquor that needs to be treated with base reduces the consumption of base considerably. Any separated aqueous phase liquor can be recycled to the fermentor or otherwise disposed of.

Alternatively, the cells can be separated completely from the aqueous ferment liquor, and the aqueous liquor recycled, sent to disposal, or treated for by-product recovery. This latter mode is desirable where the aqueous phase contains recoverable extra-cellular components, such as biopolymers or enzymes. The separated cells can be then resuspended in fresh water to make the aforesaid cell cream.

The aqueous cell cream is treated with base to adjust the pH to a range of about 7 to 10, preferably 8.5 to 10, with heating to a temperature in the range of about 65° C. to 99° C., preferably 85° C. to 99° C., for a base-treating time of about 15 to 120 minutes, preferably 30 to 60 minutes.

Suitable bases include ammonia or water soluble alkali metal and alkaline earth metal oxides, hydroxides, and carbonates, such as ammonium hydroxide, sodium hydroxide, potassium hydroxide, calcium hydroxide, potassium carbonate, and the like, and mixtures thereof.

The bases normally are employed in the form of water solutions, in as concentrated a form as is convenient. Thus, it is preferred to employ ammonia or NH$_4$OH as a commercially available concentrated solution of about 28 weight percent.

While the cells remain substantially intact in this step (lysis is not desired), the base treatment step reduces the substantially nucleic acid content of the cells. For convenience we refer to the base-treated cells as nucleic acid reduced protein, or "NARP". Thus, cells derived from an ultra-low sulfur medium "ULS", are termed by us, upon subsequent base-treatment, NARP-ULS, or nucleic acid reduced protein derived from ultra-low sulfur medium.

Following the base treatment step, the base-treated cells are separated from the aqueous alkaline liquor, such as by centrifugation. Depending upon the efficiency of centrifugation, the cells may be additionally washed with water, to facilitate removal of released nucleic acids and NH$_3$. The aqueous alkaline liquor can be recycled if suitable for use in the fermentation step for reuse thereby of the organic components therein as substrate, or augmented with further base for reuse in the base-treatment step, or sent to waste disposal, as may be necessary or suitable.

Acid-Treatment

The NARP-ULS cells from the base treatment step are admixed with water to form a cellular cream of solids content as described above.

Sufficient mineral acid is added to the cream to produce a pH of about 3 to 4.5, preferably about 3.5 to 4.2, accompanying with heating to a temperature of about 75° C. to 95° C., preferably about 80° C. to 90° C., for a time of about 15 to 120 minutes, preferably about 30 to 60 minutes. The cells remain substantially intact, hydrolysis/lysis are not desired.

Suitable are the inorganic mineral acids such as sulfuric acid, muriatic acid, phosphoric acid, and the like. The acid can be added neat, though initial dilution is preferred for concentrated acids for safety. However, with good mixing to avoid localized re-heating, the heat of dilution of concentrated acids can be useful as a source of heat in the acid-treating step.

The now acid-treated cells, termed NARP-ULS-AS (AS for acid-treated), are separated, such as by centrifugation, from the aqueous acidic liquor. The aqueous acidic liquor can be neutralized and recycled to the fermentation for reuse of organic components therein as substrate, or augmented with further acid for reuse in the acid-treatment step, or sent to waste disposal, as may be necessary.

Preferably, the separated acid-treated cells are washed with such as about 1 to 4 volumes of water per volume of packed cells to remove essentially all traces of acid prior to the next step in the process of our invention, to avoid potential equipment corrosion.

Heat-Shock Treatment

The NARP-ULS-AS cells are re-admixed with sufficient water to again form a cell cream of a cellular concentration as described supra.

The cellular cream then is subjected to a short-time heat-shock at a temperature of about 100° C. to 150° C., preferably about 130° C. to 140° C., for a time of about 30 to 200 seconds, preferably about 80 to 120 seconds.

The heat shock step can be accomplished by any suitable means such as by pumping the cream through a heated coil or tubing or heat exchanger sufficient to attain the elevated temperature short-time heat-shock treatment, preferably being pumped therethrough at elevated pressure such as about 10 to 100 psig, more preferably 20 to 50 psig. For example, ¼" to ⅜" ID stainless steel tubing coil externally heated by high pressure steam such as at 30 psig, 140° C., including convenient means to vary the tubing length and pumping rate to achieve the desired residence time, can be used, providing a suitable throughput.

Extrusion

For extrusion, the cells should be handled as a cell paste having a predominantly cells, thus a water content lower than in a cream.

The heat-shocked cells, now termed NARP-ULS-AS-HS for convenience, are reduced in water content, and, if desired, can be dried. Drying or reduction in water content, can be accomplished by spray drying, drum drying, freeze drying, or the like. For example, spray drying is employed with an inlet temperature of such as about 540° F., and an outlet temperature of such as about 210° F. The NARP-ULS-AS-HS cells are adjusted in water content or admixed with sufficient water to form a workable extrusionable paste, and containing about 15 to 40 weight percent water. The extrusion step comprises shearing the cell paste under heat and pressure.

Suitable temperatures for the extrusion treatment step can vary between about 150° F. and 400° F. (65° C. to 205° C.), with a preferred maximum temperature being about 225° F. to 275° F. (107° C. to 135° C.) to avoid degradation. The exact maximum temperature employed in a particular situation will depend, of course, on the nature of the particular cells and any additives which make up the paste. Treatment for about 30 seconds generally is of sufficient duration, although depending on the characteristics of the particular paste, the treatment can extend for as little as 10 seconds or as long as 5 minutes.

The cell paste while being heated is subjected to a shearing force which corresponds preferably to a shear rate on the order of such as about 100 rpm to 600 rpm and a torque on the order of 2000 to 20,000 grams-meter. Preferably, the cell paste is subjected to heating treatment and shearing treatment by processing in a steam-heated screw extruder, or other means. It should be understood, however, that other methods of applying a shearing force, such as roller mixing and cam and blade mixing, are suitable.

In addition to microbial cells and water, the paste also can have added thereto various additives, such as salts, oils, fats, emulsifiers, flavorings, and coloring agents, and the like, to enhance the properties of the final product.

The cell paste is extruded through a die, appropriately shaped to correspond to the desired shape of the product, and passed into a conditioning zone. Typically, the extrudate is cooled by exposure to an air stream at ambient temperatures, and incidentally also partially dehydrated, thus acquiring the desirable characteristic of retainable texture.

The product is now nucleic acid-reduced and substantially allergen-free, and is termed by us NARP-ULS-AS-HS-E. The product at this stage has low nucleic acid content, and low allergens content, and is useful for human consumption as is, particularly at a moderate level as a part of the overall protein consumption of humans.

For some single cell protein materials, however, cooling in an air stream alone is insufficient to maintain texture. Various other conditioning techniques, such as drying, sometimes are required after the single-cell protein extrudate has been passed through a cooling zone.

The extruded single-cell protein can be chopped to a suitable pellet size for use as a food as is or, after physical alteration, such as grinding, crushing, or cutting, for ease of formulation, can be used as an additive in, or compounded with other normally consumed food products such as ground meat, and the like, as a high protein and substantially allergen free supplement.

Tempering (Annealing)

In a presently preferred, though optional, step in the process of our invention, a supplementary time-tempering or time-annealing step optionally can be applied to the NARP-ULS-AS-HS-E product to further reduce allergens content.

In one mode of this further supplementary allergens-reducing step, the product NARP-ULS-AS-HS-E is held for a time of about 1 to 30 months, preferably 12 to 24 months, protected from air, such as in sealed packages.

Conveniently, the time-tempering step is conducted during natural cycles of varying ambient temperatures, such that the product is subjected to at least one high of such as about 100° F. (90° F. to 150° F.) for 5 to 30 days, and at least one low of such as about 25° F. (0° F. to 30° F.) for 5 to 30 days.

Alternatively, the time-tempering step can be conducted on an accelerated basis as long as at least one heating-cooling cycle is employed, holding at the elevated temperature at least 7 days, followed by holding at the reduced temperature at least 7 days.

The time-tempered (annealed) product is designated TT for convenience.

EXAMPLES

Examples provided are intended to assist in a further understanding of our invention. Particular materials employed, species, conditions, are intended to be further illustrative of our invention and not limitative of the reasonable scope thereof.

EXAMPLE I

Cells Grown In A Standard Medium

The following fermentation is typical of the several fermentations carried out to provide cell-containing effluent for further treatment as described in the following examples.

The continuous aerobic fermentation process was conducted in a 1500-liter fermentor operated under foam-filled conditions with a liquid volume of about 610 liters, equipped with automatic pH, temperature, and liquid level controls. Inoculation was with the yeast species *Pichia pastoris* NRRL Y-11430 (described in U.S. Pat. No. 4,261,420). Agitation was provided by two paddle-type turbines driven at 1000 rpm. The aeration rate was about 4 volumes of air (at about 38 psig and about 25° C.) per volume of aqueous ferment in the fermentor per minute. Anhydrous ammonia was added at such a rate as to maintain the pH of the fermentation mixture at about 3.5.

The aqueous mineral salts midium employed was prepared by mixing, with each liter of Bartlesville, Okla., tap water, 15.86 mL 75 weight percent $H_3PO_4$, 9.53 g $K_2SO_4$, 7.8 g $MgSO_4.7H_2O$, 0.6 g $CaSO_4.2H_2O$, and 2.6 g 85 weight percent KOH.

The trace mineral solution was prepared by mixing, for each liter of solution, 65 g $FeSO_4.7H_2O$, 20 g $ZnSO_4.7H_2O$, 3 g $MnSO_4.H_2O$, 6 g $CuSO_4.5H_2O$, 5 mL conc. $H_2SO_4$, and sufficient deionized water to make 1 liter of solution.

Methanol and the aqueous mineral salts medium in a volume ratio of about 40 to 60, respectively, were individually fed to a fermentor. The methanol feed rate was such that the methanol was the growth-limiting factor. The aqueous mineral salts medium was fed at a rate of 31.5 liters per hour and the methanol at a rate of 21 liters per hour.

The trace mineral solution plus biotin was prepared by mixing 780 mL of a trace mineral solution, 20 mL water, 200 mL methanol and 0.032 g biotin. The trace mineral solution plus biotin was fed separately from the mineral salts medium via the methanol stream at a rate of 10 mL per liter of methanol.

The fermentation was conducted at about 30° C. and at about 38 psig pressure, with an average retention time of 11.6 hours (range 10–12 hours). The cell density typically was about 128.4 g of cells per liter of fermenter effluent. The total solids content of the ferment typically was about 134.7 g per liter.

Samples of the whole culture direct-dried without separation from the medium (FM 21) and without washing (direct-drying of the aqueous ferment) showed a sulfur content of typically about 1.42 weight percent S.

For analytical purposes, samples of the resulting yeast cells were separated from the aqueous ferment (fermentation effluent) by centrifugation, washed by suspension in tap water followed by recentrifugation, dried overnight at 100° C., and weighed. On a dried basis, the yield of yeast cells typically was about 40.6 g per 100 g of methanol fed. Sulfur content typically was about 0.72 weight percent S.

The total nucleic acids were extracted from the samples with 0.5 N (normal) aqueous perchloric acid at 70° C. for 20 minutes. The nucleic acid content in the extract was determined spectrophotometrically at 260 nm (nanometers). Nucleic acid content of the dried whole cells was 6.2 weight percent.

EXAMPLE II

Cells Grown On Ultra-Low Sulfur-Media (ULS)

Additional product was prepared according to the procedure described above, except that the aqueous mineral salts medium employed was an ultra-low sulfur medium prepared by adding the following reagents, per liter of Bartlesville, Okla. tap water, 18.0 mL 75 percent $H_3PO_4$, 9.82 g 85 weight percent KOH, 3.9 g $MgSO_4.7H_2O$, 0.92 g $Mg(OH)_2$, and 0.6 g $CaSO_4.2H_2O$. This medium contained about 0.38 gram of sulfur per liter. The trace mineral solution plus biotin was prepared and fed as described above.

Cell yields and product densities obtained with this ultra-low sulfur aqueous mineral salts medium were comparable to those as described above.

Samples of the whole culture direct-dried without separation from the ULS medium and without washing (direct-drying of the aqueous ferment) showed a sulfur content of typically about 0.56 weight percent S.

Cells grown on ULS medium, separated, washed, and dried, described in Example I, showed a sulfur content typically of about 0.25 weight percent S.

Cells produced under ultra-low sulfur medium conditions (Example II) are noted as ULS hereinbelow. Cells produced employing standard media (Example I) omit the ULS designation.

EXAMPLE III

Base-Treating

Each fermentor effluent (cream), as obtained from Example I (standard medium) and Example II (ultra-low sulfur medium), each contained about 13 weight percent cells.

Each cream was adjusted to a pH of 9.0 to 9.5 with concentrated $NH_4OH$ solution, and heated to 90° C. to 95° C. for 20 to 40 minutes, and then allowed to cool to about 40° C. to 50° C.

Each resulting partially cooled alkaline suspension was centrifuged, the supernatant aqueous liquid removed and discarded. The packed wet cells were resuspended in fresh tap water, and centrifuged again. Each supernatant liquid again was discarded, and the packed wet cells were collected for further processing.

The respective materials resulting from the base-treating nucleic acid reducing step were designated as nucleic acid-reduced protein NARP from standard medium, and NARP-ULS from ultra-low sulfur medium, respectively.

The nucleic acid content of NARP was analyzed as described above and determined to be 1.1 weight percent.

EXAMPLE IV

Acid-Treating

The base-treated cells NARP and NARP-ULS from Example III each were resuspended in water to a cellular cream concentration of about 10 to 20 weight percent. The pH of each cream suspension was adjusted to 4.2 with concentrated $H_2SO_4$ and each cream suspension was heated to 85° C. for 30 minutes.

Each resulting suspension was cooled to about 30° C. to 40° C., then centrifuged, the supernatant acidic aqueous liquid removed and discarded, the packed wet cells resuspended in fresh water, and then centrifuged again. Each supernatant aqueous liquid was discarded, and the packed wet cells collected for further processing.

The respective materials resulting from the acid-treating step were designated as NARP(AS) (from NARP), and NARP-ULS(AS) (from NARP-ULS), respectively.

EXAMPLE V

Heat-Shock Treatment

A cell cream of a cellular concentration of about 10 to 20 weight percent suspension was prepared from each of the cell-wet masses obtained as described in Example IV, and heat-shocked. Each cell cream was pumped via ¼" stainless steel (316 SS) tubing through a first coil of tubing (about two feet heated length) placed in a silicone oil bath. The oil bath was maintained at about 140° C. Application pressure of about 30 psig was employed. Residence time of the cell cream in the heat bath was adjusted to about 80 seconds by varying the pumping rate and/or the length of the first tubing coil. The tubing carried the cell cream through a second coil of tubing (about two feet heated length) placed in an ice-bath for rapid cooling of the heat-shocked cell cream.

The effluent cell cream, designated respectively as NARP(AS)(HS) and NARP-ULS(AS)(HS), were checked with lead acetate papers for the presence of sulfide, a suspected cause of allergic response, and each gave negative results.

Each product then was prepared for human feeding studies by drying, either by lyophilizing or by spray drying.

Cells to be lyophilized were cooled at about $-100°$ F. to $-150°$ F. with pressure reduced to about 20 milli Torr. These conditions were maintained for about 6 to 24 hours as necessary to accomplish complete sample drying. The samples so dried contained 2 percent by weight or less of residual water.

Spray-drying was accomplished by feeding the cell cream through a rotating atomizer into a chamber where it is co-mixed with filtered inlet air at about 540° F. Cream feed rate of about 18 gallons/hour was maintained so as to achieve an outlet air temperature of about 210° F. About 7 to 11 Kg/hr of single cell protein product were obtained. The samples so dried contained about 5% by weight of residual water.

EXAMPLE VI

Extrusion

The NARP-ULS(AS)(HS) prepared by spray-drying as described in Example V was blended with water to achieve about 30% by weight moisture (714 g $H_2O$ added to 2 Kg NARP-ULS(AS)(HS) of about 95 weight percent dry cells and 5 weight percent retained moisture).

The cell paste was passed through an extruder (Brabender Model EPL-V7752 ⅜" grooved barrel, a 3:1 screw, and a 0.09" die) employing extrusion temperatures of about 95° C. to 100° C. in the first heating zone, about 175° C. in the second heating zone, and the heated die extension was maintained at about 130° C. The screw was rotated at about 140 rpm with about 15,000 g meters torque. A system pressure of 27 to 29 psig was maintained with a cell paste feeding rate of about 20 g/minute. The extruded product was designated NARP-ULS-AS-HS-E.

EXAMPLE VII

Feeding Studies

Several human feeding studies were carried out using the above-produced materials. The NARP-ULS-AS-HS-E material used in Study #5 was time-tempered (TT) for two years; while the NARP-ULS-AS-HS-E material employed in Study #6 was not annealed but was freshly prepared just prior to the feeding studies. Since several Kg of product was required for each feeding study, several batches of like product were combined for use in each Study.

Typical feeding per subject in a nutritional study was 0.35 g protein/Kg body weight or about 50 g/day of single cell protein, fed mixed with juice, juice thickened with gelatin, or formulated in cookies (Study #1), while a fixed ration of 20 to 30 g/day of product was administered in the same fashion in the tolerance studies. The results of the feeding trials, which were of varied duration, are summarized below:

TABLE I

| Study # | Test Sample | Test Duration, Days | Daily Dosage | Number of Subjects | Results GI[1] | Rash |
|---|---|---|---|---|---|---|
| 1 | Whole cells (Example I) | 18 | 20 g SCP | 48 | 4 | 4 |
| 2 | NARP(AS)(HS) | 14 | 20 g SCP | 18 | 1* | 6* |
| 3 | NARP-ULS(AS)(HS) | 25 | 20 g SCP | 28 | 0 | 5* |
| 4 | NARP-ULS(AS)(HS) | 8 | 0.35 g protein/Kg | 6 | 0 | 4* |
| 5 | Extruded NARP-ULS (AS)(HS)(E)(TT) | 10 | 0.35 g protein/Kg | 6 | 0 | 0 |

TABLE I-continued

| 6 | Extruded NARP-ULS (AS)(HS)(E) | 28 | 30 g SCP | 25 | 0 | 9*(2) |

*mild reactions
(1)Gastrointestinal reactions: nausea, vomiting, diarrhea
(2)Run 6: All 9 subjects had only relatively mild rashes. However, one subject by personal preference discontinued the study after one week, and three subjects developed rash in the third week and also discontinued. The other five subjects who developed rashes completed the study. Specific data on reactions is as follows:
Days 1-5: Unevenful
Dropped from study when reaction first noted:
Subject  Reaction 1. CH    Day 6 - IR
2. TK    Day 20 - IR, Day 24 - Q
3. KM    Day 15 - I, Day 16 - IR, Day 20 - Q
4. JI    Day 15 - I, Day 16 - IR, Day 27 - Q
Continued in the study until end:
5. JW    Day 8 - RI, Q
6. AR    Day 9 - DR, Day 27 - Q
7. LK    Day 13 - ID, Day 27 - Q
8. ST    Day 15 - DR, Q
9. KO    Day 20 - R, X(?)
D - Dryness       X(?) - Possible Excoriation
I - Itching       P - Pustules
R - Reddening     Q - Desquamation These feeding studies data, summarized in Table I, indicate that growth of single cell protein material on an ultra-low sulfur medium, followed by base-treatment, then acid treatment, a high-temperature short-time heat-treatment, and finally extrusion of the single cell material (Studies #4 and #5), result in protein products which can be fed to humans at high levels (at least half the daily protein requirement) with essentially no allergenic responses.

The results of Study #5 further indicate that time-tempering is of additional benefit in achieving a low-allergen product.

The disclosure, including data, has illustrated the value and effectiveness of our invention. The examples, the knowledge and background of the field of the invention and the general principles of biology, biochemistry, and of other applicable sciences, have formed the bases from which the broad descriptions of our invention including the ranges of conditions and the generic groups of operant components have been developed, and formed the bases for our claims here appended.

We claim:

1. A process to produce microbial cellular derived protein product which comprises the steps:
   (1) growing single cell microorganisms on ultra-low sulfur medium wherein said medium contains less than about 0.44 grams sulfur per liter of aqueous ferment, under aerobic aqueous fermentation conditions employing a carbon energy substrate;
   (2) creaming the resulting single cells in admixture with sufficient water to form a cream containing about 10 to 25 weight percent cells;
   (3) base-treating the said cream employing sufficient base to produce a pH of about 7 to 10, at a temperature of about 65° C. to 99° C., for a time of about 15 to 120 minutes;
   (4) thereafter acid-treating the base-treated cells as said cream employing sufficient acid to produce a pH of about 3 to 4.5, at a temperature of about 75° C. to 95° C., for a time of about 15 to 120 minutes;
   (5) heat-shocking the base-treated acid-treated cells as said cream at a temperature of about 100° C. to 150° C. for a time of about 30 to 120 seconds;
   (6) reducing the water content of said cream to about 15 to 40 weight percent, thereby forming a paste of said base-treated acid-treated cells; and
   (7) extruding the base-treated acid-treated heat-shocked cells as said paste at a temperature of about 65° C. to 205° C., under a pressure of about 10 to 100 psig;
   thereby producing an extruded microbial cellular derived protein product exhibiting low nucleic acid content and low alergens content toward human consumption.

2. The process according to claim 1 further comprising step (8) annealing said extruded cell product by subjecting the product to at least one high temperature cycle of about 90° F. to 150° F. for about 5 to 30 days, and at least one low temperature cycle of about 0° F. to 30° F. for about 5 to 30 days.

3. The process according to claim 1 wherein in said:
   step (3) said pH is about 8.5 to 10, said temperature is about 85° C. to 99° C., and said time is about 30 to 60 minutes;
   step (5) said heat-shock is at a temperature of about 130° C. to 140° C. for a time of about 80 to 120 seconds; and
   step (7) said extrusion is at a temperature of about 107° C. to 135° C.

4. The process of claim 3 further comprising step (8) annealing said extruded product, wherein said product is held for a time of about 1 to 30 months, protected from air, such that said product is subjected to at least one high temperature cycle of about 90° F. to 150° F. for about 5 to 30 days, and at least one low temperature cycle of about 0° F. to 30° F. for about 5 to 30 days.

5. A process as in claim 1 wherein said microbial cell is a genus of bacteria selected from the group consisting of Bacillus, Escherichia, Streptomyces, Micromonospora, Streptoverticillium, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium and Microbacterium.

6. The process of claim 1 wherein said microbial cell is a genus of fungi including yeasts selected from the group consisting of: Candida, Hansenula, Torulopsis, Saccharomyces, Pichia, Debaryomyces, Lipomyces, Cryptococcus, Nematospora, Brettanomyces, and Neurospora.

7. The extruded protein product produced by the process of claim 1 wherein said product is in the form of a pellet.

8. The annealed extruded protein product produced by the process of claim 2.

9. The extruded protein product produced by the process of claim 3.

10. The process of claim 3 further comprising step (8) annealing said extruded product by subjecting the product to at least one heating/cooling cycle of elevated temperature of about 90° F. to 150° F. for at least 7 days and of reduced temperature of about 0° F. to 30° F. for at least 7 days.

11. The process of claim 2 wherein said single cell microorganism is a *Pichia pastoris*.

12. The annealed extruded protein product produced by the process of claim 11.

13. A process to produce microbial cellular derived protein product which comprises the steps:
(1) producing single-cell microorganisms by growing a *Pichia pastoris* innoculum on ultra-low sulfur medium containing less than about 0.44 grams sulfur per liter of aqueous ferment under aerobic aqueous fermentation conditions employing carbon energy substrate;
(2) forming an aqueous cream of the resulting cells containing about 10 to 25 weight percent cells,
(3) base-treating said cream with sufficient base to produce a pH of about 7 to 10, at a temperature of about 65° C. to 99° C., for a time of about 15 to 120 minutes;
(4) thereafter acid-treating the base-treated cream with sufficient base to produce a pH of about 3 to 4.5, at a temperature of about 75° C. to 95° C., for a time of about 15 to 120 minutes;
(5) heat-shocking the base-treated acid-treated cream at a temperature of about 100° C. to 150° C., for a time of about 30 to 120 seconds;
(6) preparing a paste of said base-treated acid-treated heat-shocked cells to contain about 15 to 40 weight percent water;
(7) extruding said paste at a temperature of about 65° C. to 205° C., under a pressure of about 10 to 100 psig; and
(8) time-tempering the extruded nroduct from said step (7) for a time of about 1 to 30 months, protected from air, such that said product is subjected to at least one high temperature cycle of about 90° F. to 100° F. for about 5 to 30 days, and at least one low temperature cycle of about 0° F. to 30° F. for about 5 to 30 days;
thereby preparing an extruded protein product of reduced nucleic acid content and substantially allergens free content for human consumption.

14. The tempered extruded protein product produced by the process of claim 13.

* * * * *